United States Patent
Everson et al.

(10) Patent No.: US 6,484,734 B1
(45) Date of Patent: Nov. 26, 2002

(54) MULTI-STEP POST DETERGENT TREATMENT METHOD

(75) Inventors: Terrence P. Everson, Eagan, MN (US); Shaun P. Kennedy, North Oaks, MN (US); Charles A. Hodge, Cottage Grove, MN (US)

(73) Assignee: Ecolab Inc., St. Paul, MN (US)

( * ) Notice: Subject to any disclaimer, the term of this patent is extended or adjusted under 35 U.S.C. 154(b) by 0 days.

(21) Appl. No.: 09/353,706

(22) Filed: Jul. 14, 1999

(51) Int. Cl.⁷ .................................................. B08B 3/04
(52) U.S. Cl. ........................... 134/25.2; 134/3; 134/41; 134/26; 134/29; 134/36; 510/514; 510/521; 510/522; 510/524
(58) Field of Search .............................. 134/25.2, 3, 41, 134/26, 29, 36; 510/514, 521, 522, 524

(56) References Cited

U.S. PATENT DOCUMENTS

| | | | |
|---|---|---|---|
| 3,635,827 A | * 1/1972 | Jakobi | 510/220 |
| 4,501,681 A | 2/1985 | Groult et al. | 252/174.12 |
| 5,056,542 A | 10/1991 | Reinhard | 134/57 |
| 5,131,419 A | 7/1992 | Roberts | 134/50 |
| 5,232,622 A | 8/1993 | Jones et al. | 252/174.24 |
| 5,282,901 A | 2/1994 | Reinhard | 134/18 |
| 5,320,118 A | 6/1994 | Fernholz | 134/93 |
| 5,429,679 A | 7/1995 | Young, Jr. | 134/25.2 |
| 5,447,648 A | 9/1995 | Steindorf | 252/90 |
| 5,448,115 A | 9/1995 | Howland et al. | 307/118 |
| 5,453,216 A | * 9/1995 | Kellet | 134/25.2 |
| 5,501,742 A | 3/1996 | Fernholz | 134/25.2 |
| 5,578,134 A | * 11/1996 | Lentsch et al. | 134/25.2 |
| 5,589,099 A | 12/1996 | Baum | 510/514 |
| 5,603,776 A | * 2/1997 | Lentsch et al. | 134/25.2 |
| 5,759,988 A | 6/1998 | Heile et al. | 510/441 |
| 5,876,514 A | 3/1999 | Rolando et al. | 134/25.2 |
| 5,879,469 A | 3/1999 | Avram | 134/25.2 |

* cited by examiner

Primary Examiner—Sharidan Carrillo
(74) Attorney, Agent, or Firm—Merchant & Gould P.C.

(57) ABSTRACT

Thus use of a post detergent step for removing aqueous residue from ware combined with a subsequent step using a potable rinse or a dilute solution of an aqueous food grade rinse aid to rinse alkaline washed ware provides significant advantages. The two step rinse method insures complete and sanitary cleaning of ware while permitting the use of different formulations in the post detergent step and the subsequent rinse step. Such process conditions permit the use of differing times and temperatures in the post detergent step and in the rinse step and permits the use of different formulations in the post detergent step and in the rinse step.

9 Claims, No Drawings

MULTI-STEP POST DETERGENT TREATMENT METHOD

FIELD OF THE INVENTION

The invention relates to cleaning and rinsing ware in institutional or industrial automatic warewashing machines. More particularly, the invention involves post detergent treatments and rinsing steps for ware that is first cleaned using alkaline detergents leaving clean ware with an alkaline detergent residue on the ware surface. The clean ware is then processed in a procedure involving a post detergent step and a rinse step. The post detergent step involves the use of an aqueous solution of surfactant or chemical rinse additive or agent that can remove a substantial proportion of previously formed detergent residue. This step can leave some amount, typically a small but measurable proportion of rinse aid, food, surfactant, detergent or a combination residue. A subsequent rinse step uses an aqueous potable rinse or an aqueous dilute solution of food grade surfactant to complete the cleaning method and substantially remove such remaining residue.

BACKGROUND OF THE INVENTION

The use of automatic warewashing machines to clean and rinse ware has been known for many years. Fernholz et al., U.S. Reissue Pat. Nos. 32,818 and 32,763 disclose the use of solid block alkaline cleaning compositions and subsequently rinsing alkaline residues from clean ware. Commonly, after ware is cleaned using alkaline detergents, the ware is often rinsed using a dilute aqueous solution of a typically synthetic polymeric composition comprising at least a block of ethylene oxide in combination with other moieties in the composition to result in an aqueous composition that can cause the rapid sheeting of the rinse water from ware for the intended purpose of leaving a bright, clean, unspotted product. These polymeric materials are typically called rinse aid agents. When dissolved in water a rinse agent forms a rinse solution or composition that, because of the surface energy of the ware and the relationship between the rinse aid and the surface energy, causes sheeting. Warewashing and rinsing processes have been embodied in a variety of institutional and industrial automatic warewashing machines that have automatic control mechanisms that expose ware to a variety of prescraping, scraping, prerinse, alkaline wash, acid wash, rinse, sanitize, post-sanitize, etc. steps. Particularly in large, high volume, multistep warewashing machines, the sequence of steps can be programmed to achieve a desired result.

A variety of cleaning and rinsing processes are known, including Avram, U.S. Pat. No. 5,879,469, which teaches a warewashing system using a basic aqueous wash followed by an acidic aqueous wash. Howland et al., U.S. Pat. No. 5,448,115, shows that aqueous rinse cycles can be effectively controlled to modify dispensing and timing of cleaning chemicals. Young, Jr. et al., U.S. Pat. No. 5,429,679, shows further control systems and in particular directing rinse water recycle into other washing cycle steps. Steindorf, U.S. Pat. No. 5,447,648, and Baum, U.S. Pat. No. 5,589,099, disclose solid food grade rinse aid compositions and improved synthetic ethylene oxide propylene oxide block copolymer based rinse aids. Groult et al., U.S. Pat. No. 4,501,681, show at Column 8, lines 35–55 and elsewhere, the use of multiple rinse steps. Groult et al. appear to show a process involving a first and second rinse step using rinse water followed by a third rinse step using acid or neutral rinsing agents. Jones et al., U.S. Pat. No. 5,232,622, show two sequential rinse steps (Column 6, lines 49–64). Jones et al. disclose nothing regarding the compositions used in the rinse cycles, however, the cycles likely contain conventional synthetic alkaline oxide based rinse agents.

Haslop et al., U.S. Pat. No. 4,618,446, discloses ingredients for use in spherical liquid detergent compositions. Haslop et al., U.S. Pat. No. 4,793,943, teaches a variety of ingredients useful for making liquid detergent compositions. Akred et al., U.S. Pat. No. 4,871,467, teaches a variety of compositions and materials used to form non sedimenting liquid detergent compositions. Aronson et al., U.S. Pat. No. 5,045,225, teaches a combination of hydrocarbon oils and silicone compositions as antifoam materials. Gentle et al., U.S. Pat. No. 5,073,298, teaches silicone silicate based defoaming compositions. Chun et al., U.S. Pat. No. 5,133,892, teaches machine dishwashing detergent tablets having timed release of enzyme and chlorine bleach and a variety of other ingredients used in making the detergent composition.

Tsukada, Japanese Patent Application Publication Kokai 49-126,703, teaches carbohydrate aliphatic ester rinse agents. Miura et al., Japanese Patent Application Publication Kokai 50-62,211, teaches polyhydric alcohol containing rinse agents. Miura et al., Japanese Patent Application Publication Kokai 51-68,608, teaches polyol aliphatic ester containing rinse agent compositions. Suzuki et al., Japanese Patent Application No. 86-131,272, teaches a rinse agent comprising a polyethoxylated sorbitan fatty acid ester glycerol and a sugar alcohol. Suzuki et al., Japanese Patent Application No. 86-161,193, teaches a similar material. Nantaku, Japanese Patent Application No. 59-187,096, teaches a polyglycerine ester of a $C_6$-8 fatty acid containing rinse agent. Wilson et al., "Rinse Additives for Machine Dishwashing", *Soap and Chemical Specialties*. pp. 48 et seq. (February 1958), discusses the basic technology regarding rinse agent formulation. The use of a rinse composition often remove substantial amounts of alkaline residue but can leave some proportion of food residue and some amount of rinse agent residue.

The use of a food grade rinse aid has attracted increasing attention over recent years. Such surfactants are attractive to people requesting more natural chemical materials in warewashing processes. These food grade rinse aids commonly comprise sucrose fatty acid esters, sorbitan fatty acid esters, glycerol fatty acid esters and other similar materials comprising a natural polyol or polymerized polyol derivatized with one or more fatty acid or other natural hydrophobic moiety. Depending on the nature of the ware, the type and content of soil, the hardness of service water, the temperature of washing, and other variables, a food grade rinse aid often provide a level of rinsing which does not meet or exceed the level of rinsing obtained from synthetic polyalkylene oxide type rinse agents.

While the level of activity of the food grade rinse agent is typically acceptable to most operators, a synthetic polyalkylene oxide rinse aid provide a level of sheeting at an effective concentration that is superior to food grade rinse aids. Further, in many kitchens, a strong desire to use food grade rinse aids in a final stage is evident while the use of a synthetic polyalkylene oxide based rinse aid are not desirable in a final step.

Accordingly, a substantial need exists for warewashing methods that can obtain the advantages of conventional rinsing cycles with desired performance while also obtaining the advantages of food grade rinse aid compositions. Such benefits include clean, well rinsed ware with no residue, spotting or streaking.

SUMMARY OF THE INVENTION

We have found improved warewashing methods involving cleaning ware with an alkaline detergent producing clean ware, leaving aqueous alkaline residue, followed by a post detergent regimen. In the post detergent regimen, the clean ware is then contacted with a first aqueous post detergent step using an aqueous composition. The aqueous composition comprises a rinse composition having a rinse agent with a polyalkylene oxide moiety to remove the alkaline residue producing treated ware. The treated ware is then contacted in a rinse step with a rinse composition comprising either a food grade rinse agent or an aqueous or potable water rinse, said aqueous or potable water rinse is substantially free of a synthetic rinse agent, for at least three seconds. To ensure complete sanitization of the ware, a sanitation step is used prior to the post detergent regimen. Such a step can include any technique that reduces the numbers of pathogens to a sanitizing level. Preferably, the method uses a biocide or an elevated aqueous rinse temperature to achieve sanitized ware or both.

Accordingly, the invention is found in a method of cleaning ware involving a first cleaning step using an aqueous alkaline cleaning composition, resulting in cleaned ware having an alkaline residue. The cleaned ware is then contacted with an aqueous composition in post detergent step, the aqueous composition comprising about 10 to 500 ppm, of a synthetic nonionic sheeting agent comprising a polyalkylene oxide moiety, to form treated ware. The method further comprises contacting the treated ware with an aqueous rinse composition; wherein the cleaning method also includes a post detergent sanitizing step.

The invention is also found in a method of cleaning ware involving a first cleaning step using an aqueous alkaline cleaning composition, resulting in cleaned ware having an alkaline residue. The cleaned ware is then contacted with an aqueous composition in a post detergent step, the aqueous composition comprising about 10 to 500 ppm, of a synthetic nonionic sheeting agent comprising a polyalkylene oxide moiety, to form treated ware. The method further comprises contacting the treated ware with an aqueous rinse composition comprising about 1 to 800 ppm of a combination of a food grade sheeting agent and a solubility agent; wherein the cleaning method also includes a post detergent sanitizing step.

DETAILED DISCUSSION OF THE INVENTION

The warewashing process of the invention includes an alkaline washing step, a first post detergent step and a rinse step. In the alkaline warewashing step, the ware is contacted with an alkaline aqueous cleaning solution that removes food soils from the ware surface. The alkaline step, which leaves minor alkaline residue on the surface of the ware, is followed by a post detergent step in which the ware is contacted with an aqueous solution of a rinse agent in a rinse composition that is designed to substantially remove the alkaline residue, preferably leaving clean unspotted ware. However, such steps can leave some small food and rinse agent residue on the ware surface. The ware, after the post detergent step, is contacted with an aqueous rinse. Such a rinse can comprise a composition as simple as a potable water rinse or can comprise a rinse composition containing a food grade rinse agent at an effective concentration.

The post detergent step can contain rinse agents that are conventional rinse agents containing a polyalkylene, preferably a polyethylene oxide moiety, while the rinse step can contain a food grade rinse agent, typically comprising a soya phospholipid, a sugar fatty acid ester such as a glucose or sucrose fatty acid ester, a sorbitan fatty acid ester, a $C_2$–$C_4$ polyol fatty acid ester or a soya phospholipid or mixtures thereof. An effective post detergent rinse composition or other rinse composition commonly is tested for sheeting and low foaming properties. Sheeting is typically tested using substantially subjective visual testing determining whether the ware completely sheets or leaves some type of residue. Rinse agent foaming is tested using a foaming apparatus and method set forth in Steindorf, U.S. Pat. No. 5,447,648 at Column 9, line 1 through Column 11, line 3.

There are two general types of detergent/rinse cycles in commercial warewashing machines. A first type, a sanitizing cycle, uses sanitizing water at least about 180° F. (about 82° C. or higher) for at least 3 seconds. A second type in non-sanitizing machines use lower temperature non-sanitizing rinse water. Typically, the temperature of the service water available, from the water heaters installed at the use location, is about 125° F. (about 52° C.), 140° F. (about 160° C.), 60° F. (about 71° C.), etc. A surfactant useful in any of these use locations is an aqueous rinse can have a cloud point greater than the available hot service water. For the purpose of this invention, the term "rinse agent" includes concentrate materials that are diluted with an aqueous stream to produce an aqueous rinse.

Accordingly, an aqueous rinse agent is an aqueous material that is contacted with ware in a rinse cycle. A sheeting agent is the polymeric material used to promote the even drainage of the aqueous rinse. Sheeting is defined as forming a continuous, evenly draining film, leaving virtually no spots or film upon the evaporation of water. For the purpose of this invention, the term "dish" or the term "ware" is used in the broadest sense of the term to refer to various types of articles used in the preparation, serving, consumption, and disposal of foodstuffs including pots, pans, trays, pitchers, bowls, plates, saucers, cups, glasses, forks, knives, spoons, spatulas, and other glass, metal, ceramic, plastic composite articles commonly available in the institutional or household kitchen or dining room.

Biocides

Biocides can be used in a sanitizing step. Biocides are antimicrobial agents or chemical compositions that can prevent microbiological contamination or deterioration caused by microorganisms. Most useful antimicrobial agents comprise phenolics, halogen compounds, quaternary ammonium compounds, amines, alkanol amines, nitro compounds and a variety of miscellaneous types of antimicrobial agents. Antimicrobial agents operate by either interfering with a cellular mechanism or a cellular component of the microbe resulting in the substantial reduction of microbial populations or simply prevent proliferation in numbers of microorganisms that would prevent the accumulation of harmful numbers of microorganisms. Antimicrobial agents are often effective against one or more of typical microbial classifications such as gram positive, gram negative, fungi, molds and yeasts.

The preferred antimicrobial agent used to kill or reduce microbial populations requires physical and chemical compatibility with the system, stability and resistance to be inactivated by other components or ingredients in this system, stability under use and storage conditions of pH temperature and light exposure while being safe and essentially non-toxic to humans in handling formulation and use. Typical antimicrobial agents are used in aqueous solution at a concentration of about 0.1 to 1000 ppm, preferably about 1 to 200 ppm and are simply contacted with the ware in a separate step or as a component of the post detergent rinse or the final aqueous rinse step of the invention. Preferred antimicrobial agents for use in the invention for sanitizing the surface of ware include the following classes of compounds Biocides are antimicrobial agents or chemical compositions that can prevent microbiological contamination or deterioration caused by microorganisms. Most useful antimicrobial agents comprise phenolics, halogen compounds, quaternary ammonium compounds, amines, alkanol amines, nitro compounds and a variety of miscellaneous types of antimicrobial agents. Antimicrobial agents operate by either interfering with a cellular mechanism or a cellular component of the microbe resulting in the substantial reduction of microbial populations or simply prevent proliferation in numbers of microorganisms that would prevent the accumulation of harmful numbers of microorganisms. Antimicrobial agents are often effective against one or more of typical microbial classifications such as gram positive, gram negative, fungi, molds and yeasts.

The preferred antimicrobial agent used to kill or reduce microbial populations requires physical and chemical compatibility with the system, stability and resistance to be inactivated by other components or ingredients in this system, stability under use and storage conditions of pH temperature and light exposure while being safe and essentially non-toxic to humans in handling formulation and use. Typical antimicrobial agents are used in aqueous solution at a concentration of about 0.1 to 1000 ppm, preferably about 1 to 200 ppm and are simply contacted with the ware in a separate step or as a component of the post detergent rinse or the final aqueous rinse step of the invention.

Post Detergent Rinse

The use of nonionic surface active agents for rinse agents and rinse compositions include typically synthetic organic molecules including at least a polyoxyethylene group. Preferred agents for use in this invention include polyoxyethylene/polyoxypropylene/polyoxyethylene block copolymers, polyoxypropylene/polyoxyethylene/polyoxypropylene block copolymers and alkalethoxylate polymeric materials. Such materials have the following formulae:

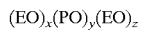(EO)$_x$(PO)$_y$(EO)$_z$

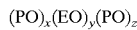(PO)$_x$(EO)$_y$(PO)$_z$

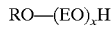RO—(EO)$_x$H wherein R is a $C_6$–$C_{24}$ alkyl or a $C_6$–$C_{24}$ alkyl substituted phenol moiety, EO comprises ethylene oxide, PO comprises propylene oxide and x, y and z reflect the average molecular proportion of each alkylene oxide moiety in the overall polymer composition. In this, x typically ranges from about 10 to about 130, y typically ranges from about 10 to about 70, while z typically ranges from about 10 to about 130, and x plus y is typically greater than about 60. The total polyoxyethylene moiety of each polymeric material constitutes typically at least about 40 mole %, commonly at least 75 mole %. These polymeric rinse agent materials preferably have a molecular weight greater than about 5000, more preferably greater than about 10,000. In a preferred embodiment, the post detergent rinse step comprises about 10 to 500 ppm of a synthetic nonionic sheeting agent comprising a polyalkylene oxide moiety.

Food Grade Rinse

The second rinse step can comprise potable water, either with or without inclusion of a suitable food grade rinse agent. Preferred food grade rinse agents include sucrose fatty acid ester, a sorbitan fatty acid ester, a glycerol fatty acid ester, a propylene glycol fatty acid ester, a soya phospholipid, or mixtures thereof. The second rinse step may also include such components as a solubility agent and an acidity source. If so, the solubility agent is preferably present at a concentration of about 1 to 400 ppm and the acid is preferably present at a concentration of about 0.01 to 25 ppm.

In a preferred embodiment, the aqueous rinse composition comprises a surfactant composition comprising 1 to 250 ppm of a sucrose fatty acid ester, about 1 to 320 ppm of a solubility agent. In one embodiment, the solubility agent comprises ethanol, propylene glycol, glycerol or mixtures thereof. Preferably, the aqueous rinse has a pH of less than 7. In another preferred embodiment, the food grade sheeting agent comprises a sucrose fatty acid ester, a sorbitan fatty acid ester, a glycerol fatty acid ester, a propylene glycol fatty acid ester, a soya phospholipid, or mixtures thereof. Preferably, the food grade sheeting agent is used at a concentration of about 20 to 300 ppm, more preferably about 25 to 150 ppm.

To meet the requirements of particular Asian markets, the post detergent step is preferably conducted for at least three seconds. Likewise, the rinse step involving potable water alone or in combination with a food grade sheeting agent is carried out for about 3 to 7 seconds, preferably about 4 to 6 seconds. Preferably, the aqueous rinse composition consists essentially of potable water.

Sorbitan Aliphatic Esters

Sorbitan aliphatic esters suitable for use in the rinse aid composition include any sorbitan aliphatic ester capable of providing effective foam control and cooperating with the other components for producing a solid nose aid composition. One group of particularly suitable sorbitan aliphatic esters are the sorbitan fatty acid esters. Sorbitan fatty acid esters can provide effective sheeting action and rinsing performance. Sorbitan fatty acid esters suitable for the use in the rinse aid composition include mono-, di-, tri- and tetra-esters and mixtures thereof. Sorbitan fatty acid esters may be derived by esterification of sorbitol with such fatty acids as lauric, myristic, palmitic, stearic, oleic, linolic, and similar saturated and unsaturated, branched and straight chain fatty acids. Preferably, the fatty acids are $C_{6-24}$ straight chain fatty acids having less than 3 unsaturated carbon bonds.

Based upon cost, availability and ability to provide excellent sheeting action and rinsing performance, the preferred useful sorbitan fatty acid esters include monoesters such as sorbitan monocaprylate acid, sorbitan monolaurate, sorbitan monopalmitate, sorbitan monostearate, sorbitan monooleate, sorbitan monolinoleate, sorbitan mono eleostearate, sorbitan monopentadecanoic acid ester, sorbitan monoheptadecanoate; diesters such as sorbitan sesquistearate and sorbitan sesquioleate; tri esters such as sorbitan tristearate and sorbitan trioleate. Because of the difficulty encountered in attempting to purify sorbitan fatty acid esters from the reaction mixture, the sorbitan fatty acid ester will typically contain various amounts of sorbitol fatty acid ester(s), sorbide fatty acid ester(s) and trace quantities of sorbitan, sorbitol, sorbide and fatty acid(s). Sorbitan fatty acid esters containing such "contaminants" may be effectively employed in the rinse aid composition without significant adverse effect.

Sucrose Aliphatic Esters

Sucrose aliphatic esters suitable for use in the rinse aid composition include any sucrose aliphatic ester capable of contributing to the sheeting action and rinsing performance of the composition and cooperating with the other components for producing a solid rinse aid composition. Sucrose has a total of eight reactive hydroxyl groups which are subject to substitution. One group of particularly suitable sucrose aliphatic esters are the sucrose fatty acid esters which are generally solid at room temperature and can also assist in solidifying the composition. The sucrose fatty acid esters suitable for the use in the rinse aid composition include mono to octa-fatty acid esters and mixtures thereof. Sucrose fatty acid esters may be derived by esterification of sucrose with such saturated fatty acids as acetic, propionic, butyric, valeric, caproic, enanthic, caprylic, pelargonic, capric, lauric, myristic, palmitic, and stearic; unsaturated fatty acids such as palmitoleic, oleic, vaccenic, linoleic, sorbic, linolenic, and arachidonic and similar saturated and unsaturated, branched and unbranched fatty acids. Sucrose fatty acid esters are readily available from a number of sources including Mitsubishi-Kasei Foods Corporation of Tokyo, Japan under the designation Ryoto Sugar Esters, and Dai-ichi Kogyo Seiyaku Company Ltd. of Tokyo, Japan.

The preferred sucrose fatty acid ester for use in the rinse aid composition is a mixture of about 2 to about 12 wt % sucrose laurate and about 25 to about 85 wt % sucrose palmitate. Such a materials provides effective sheeting action and rinsing performance while contributing to the formation of a solid product with beneficial dispensing characteristics. The sucrose laurate and sucrose palmitate may be provided as monoesters, diesters, triesters, tetraesters, pentaesters, hexaesters, heptaesters, octaesters and mixtures thereof. However, the shelf life and performance of the of the rinse aid composition is enhanced when at least about 70% of the sucrose palmitate is a monoester and at least about 80% of the sucrose laurate is a monoester.

Polyglycerol Aliphatic Esters

Polyglycerol aliphatic esters suitable for use in the rinse aid composition include any polyglycerol aliphatic ester capable of contributing to the sheeting action and rinsing performance of the composition and cooperating with the other components for producing a solid rinse aid composition. One group of particularly suitable polyglycerol aliphatic esters are the polyglycerol fatty acid esters. Suitable polyglycerol fatty acid esters include specifically, but not exclusively, those derived by esterification of a polyglycerol with such saturated fatty acids as acetic, propionic, butyric, valeric, caproic, enanthic, caprylic, pelargonic, capric, lauric, myristic, palmitic, and stearic; unsaturated fatty acids such as palmitoleic, oleic, vaccenic, linoleic, sorbic, linolenic, and arachidonic; and similar saturated and unsaturated, branched and unbranched fatty acids. Polyglycerol fatty acid esters are readily available from a number of sources including Nikko Chemicals Company, Ltd of Tokyo, Japan, and Toho Chemical Industry Company, Ltd. of Tokyo, Japan. Because of the relatively low cost, ready availability, sheeting performance, and ability to provide a rinse aid composition with beneficial dispensing characteristics, the preferred polyglycerol fatty acid ester for use in the rinse aid composition is decaglycerol monolaurate available from Nikko Chemicals Company, Ltd of Tokyo, Japan. The polyglycerol aliphatic ester may be effectively used within the rinse aid composition at a concentration of about 2 to about 20 wt %.

Optional Polyol Fatty Acid Esters

The food grade rinse aids of the invention may also contain one or more additional food grade fatty acid esters of other polyols such as glycerol, glycerol, diglycerol, triglycerol, glyceraldehyde, erythrose, threose, ribose, arabinose, xylose, glucose, mannose, galactose, ribulose, xylose, fructose, lactose, maltose, cellobiose, and the like. Such polyol fatty acid esters are useful for contributing to the sheeting action and rinsing performance of the composition and cooperating with the other components for producing a useful rinse aid composition.

Defoaming Agents

Defoaming agents (defoamers) include a variety of different materials adapted for defoaming a variety of compositions. Defoamers can comprise an anionic or nonionic material such as polyethylene glycol, polypropylene glycol, fatty acids and fatty acid derivatives, fatty acid sulfates, phosphate esters, sulfonated materials, silicone based compositions, and others.

Preferred defoamers are food additive defoamers including silicones and other types of active anti-foam agents. For the purposes of this application, the term "food additive" means materials listed in the U.S. Code of Federal Regulations 21 Part 172—Food Additives Permitted for Direct Addition to Food for Human Consumption, 21 Part 182—Substance Generally Recognized as Safe and 21 Part 184—Direct Food Substances A:ffired as Generally Recognized as Safe, and 21 Part 173—Secondary Direct Food Additives Permitted in Food for human Consumption, Section 173.310.

Silicone foam suppressers include polydialkylsiloxane preferably polydimethylsiloxane. Such silicone based foam suppressers can be combined with silica. Such silica materials can include silica, fumed silica, derivatized silica, silanated silica, etc. Commonly available anti-foaming agents combines a polydimetbylsiloxane and silica gel. Another food additive defoaming agent comprises a fatty acid defoamer. Such defoamer compositions can comprise simple alkali metal or alkaline earth metal salts of a fatty acid or fatty acid derivatives. Examples of such derivatives include mono, di- and tri-fatty acid esters of polyhydroxy compounds such as ethylene glycol, glycerol, Propylene glycol, hexylene glycol, etc. Preferably such defoaming agents comprise a fatty acid monoester of glycerol. Fatty acids useful in such defoaming compositions can include any $C_{6-24}$ saturated or unsaturated, branched or unbranched mono or polymeric fatty acid and salts thereof, including for example myristic acid, palmitic acid, stearic acid, behenic acid, lignoceric acid, palmitoleic acid, oleic acid, linoleic acid, arachidonic acid, and others commonly available. Other food additive anti-foam agents available include water insoluble waxes, preferably microcrystalline wax, petroleum wax, synthetic petroleum wax, rice base wax, beeswax having a melting point in the range from about 35° to 125° C. with a low saponification value, white oils, etc. Such materials are used in the rinse agents of the invention at a sufficient concentration to prevent the accumulation of any measurable stable foam within the dish machine during rinse cycle.

Food Grade Fillers

The food grade rinse aid composition of the invention can contain one or more solid water soluble food grade fillers for the purpose of facilitating processing, product stability, or dispensing of the composition or contributing to other performance characteristics. Many different types of fillers may be utilized in the rinse agent composition, including specifically but not limited to such compounds as a sugar such glucose, fructose, sucrose; an alkali metal salt such as sodium chloride, potassium chloride, sodium carbonates, sodium bicarbonate, sodium sulfate, potassium sulfate, sodium acetate, sodium lactate, water soluble amino acids such as alanine, arginine, glycine, lysine, proline; phosphates such as tetrasodium pyrophosphate, sodium phosphate and others.

Chelating Agents

The rinse agents of the invention can contain a complexing or chelating agent that aids in reducing the harmful effects of hardness components in service water. Typically calcium, magnesium, iron, manganese, and other polyvalent metal cations present in service water, can interfere with the action of either washing compositions or rinsing compositions. A chelating agent can effectively complex with and prevent such ions from the service water interfering with the action of an active component increasing rinse agent performance. Both organic and inorganic chelating agents are common. Inorganic chelating agents include such compounds as sodium pyrophosphate, and sodium tripolyphosphate while organic chelating agents include both polymeric and small molecule chelating agents. Polymeric chelating agents commonly comprise ionomer compositions such as polyacrylic acids compounds. Small molecule organic chelating agents include salts of ethylenediaminetetracetic acid (EDTA) and hydroxyethylene-diaminetetracetic acid, nitrilotriacetic acid, ethylenediaminetetrapropionates, triethylene-tetraminehexacetates, and the respective alkali metal ammonium and substituted ammonium salts thereof. Amino phosphates are also suitable for use as chelating agents in the composition of the invention and include ethylenediamine tetra(methylene-phosphonate), nitrilotrismethylenephosphonate, diethylenetriaminepenta (methylene phosphonates). These amino phosphonates commonly contain alkyl or alkylene groups with less than 8 carbon atoms. Preferred chelating agents for this invention include approved food additive chelating agents such as the disodium salt of ethylenediamine-tetracetic acid.

Solubility Agents

Solubility aids or agents can be used to enhance the water solubility of the food grade sheeting agents used in the invention. Preferred solubility agents include ethanol, propylene glycol, glycerine and mixtures thereof.

Liquid Carriers

The liquid rinse agents of the invention can have a liquid base component which functions as a carrier and cooperates with aqueous diluents to form the aqueous rinse. Liquid bases are preferably water or a solvent compatible with water to obtain compatible mixtures thereof. Exemplary nonlimiting solvents in addition to water include a low molecular weight $C_{1-6}$ primary and secondary mono, di- and tri- hydroxy alcohol such as methanol, ethanol, isopropanol, and polyols containing from two to six carbon atoms and from two to six hydroxyl groups such as propylene glycol, ethylene glycol, glycerine, propane diol, propylene glycol, etc.

Other Components

The organic nature of the rinse agents of the invention can be subject to microbial and chemical decomposition. Organic materials are commonly useful in stabilizing the mixtures. Preferred preservatives or stabilizers for the invention include food grade stabilizers, food grade antioxidants, etc. Most preferred materials for use in stabilizing the compositions of the invention include $C_{1-10}$ mono, di- and tricarboxylic acid compounds. Preferred examples of such acids include acetic acid, citric acid, benzoic, sorbic, lactic, maleic, tartaric and fumaric. Optional ingredients which can be included in the rinse agents of the invention in conventional levels for use include solvents, hydrotropes, processing aids, corrosion inhibitors, dyes, fillers, optical brighteners, germicides, pH adjusting agents (monoethanolamine, sodium carbonate, sodium hydroxide, hydrochloric acid, phosphoric acid, et cetera), bleaches, bleach activators, perfumes and the like.

The compositions of the invention can be formulated using conventional formulating equipment and techniques. The compositions of the invention typically can comprise proportions as set forth in Table 1. In the manufacture of the liquid rinse agent of the invention, typically the materials are manufactured in commonly available mixing equipment by charging to a mixing chamber the liquid diluent or a substantial proportion of a liquid diluent. Into a liquid diluent is added preservatives or other stabilizers. Care must be taken in agitating the rinse agent as the formulation is completed to avoid degradation of polymer molecular weight or exposure of the composition to elevated temperatures. The materials are typically agitated until uniform and then packaged in commonly available packaging and sent to distribution center before shipment to the consumer.

TABLE 1

Liquid Rinse Agent Proportions (wt %)

| Ingredient | Useful | Preferred | Most Preferred |
|---|---|---|---|
| Sheeting surfactant(s) | 1–65 | 2–60 | 3–50 |
| Defoamer | 0.1–10 | 0.2–8 | 0.5–5 |
| Biocide | 0.001–2 | 0.002–1 | 0.003–3 |
| Hydrotrope | 0.1–25 | 0.2–20 | 0.3–15 |
| Solvent | 0.1–25 | 0.2–20 | 0.3–15 |
| Water | Bal. | Bal. | Bal. |

The liquid materials of the invention can be adapted to a cast solid format by incorporating into the composition a casting agent. Typically organic and inorganic solidifying materials can be used to render the composition solid. Preferably organic materials are used because inorganic compositions tend to promote spotting in a rinse cycle. The most preferred casting agents are polyethylene glycol and an inclusion complex comprising urea and a nonionic polyethylene or polypropylene oxide polymer. Polyethylene glycols (PEG) are used in melt type solidification processing by uniformly blending the sheeting agent and other components with PEG at a temperature above the melting point of the PEG and cooling the uniform mixture. An inclusion complex solidifying scheme is set forth in Morganson et al., U.S. Pat. No. 4,647,258.

The solid compositions of the invention are set forth in Table 2 as follows:

TABLE 2

Solid Rinse Agent Proportions (wt %)

| Ingredient | Useful | Preferred | Most Preferred |
|---|---|---|---|
| Sheeting surfactant(s) | 1–65 | 2–60 | 3–50 |
| Defoamer | 0.1–10 | 0.2–8 | 0.5–5 |
| Biocide | 0.001–2 | 0.002–1 | 0.003–3 |
| Hydrotrope | 0.1–25 | 0.2–20 | 0.3–15 |
| Solvent | 0.1–25 | 0.2–20 | 0.3–15 |
| Solidifying agent | 1–25 | 2–20 | 3–15 |

Liquid rinse agents are dispensed by incorporating compatible packaging containing the liquid material into a dispenser adapted to diluting the liquid with water to a final use concentration wherein the active material is present in the aqueous rinse at a concentration of 20 to 500 parts of the active block copolymer per million parts of the aqueous rinse. More preferably the material is present in the aqueous rinse at a concentration of about 30 to 300 parts of the block copolymer per million parts of the aqueous rinse most preferably the material is present at a concentration of about 40 to 200 parts of the block copolymer per million parts of the aqueous rinse. Examples of dispensers for the rinse of the invention are DRYMASTER-P sold by Ecolab Inc. Cast solid may be conveniently dispensed by inserting a cast solid material in a container or with no enclosure into a spray-type dispenser such as the volume SOL-ET controlled Rinse Injection Cylinder system manufactured by Inc., St. Paul, Minn. Such a dispenser cooperates with a warewashing machine in the rinse cycle. When demanded by the machine, the dispenser directs a spray of water onto the cast solid block of rinse agent which effectively dissolves a portion of the block creating a concentrated aqueous rinse solution which is then fed directly into the rinse water forming the aqueous rinse. The aqueous rinse is then contacted with the dishes to affect a complete rinse. This dispenser and other similar are capable of controlling the effective concentration of the active block copolymer in the aqueous rinse by measuring the volume of material dispensed, the actual concentration of the material in the rinse water (an electrolyte measured with an electrode) or by measuring the time of the spray on the cast block.

The following examples and data further illustrate the practice of the invention, should not be taken as invention and contains the best mode. The following examples and data show the effectiveness of the invention in promoting adequate rinsing.

Experimental Section

A high temperature automatic door machine, a Hobart AM-14 used for the test, was modified to accommodate a second rinse water line in which a second or separate rinse additive could be introduced to the modified the rinse cycle. For the purpose of this patent disclosure, the additives will be distinguished by calling the first additive a post detergent composition while the second additive will be a food grade rinse additive or water.

Two rinse additive programmable pumps were installed in parallel such that one pump would function as the other was inactive. The pumps were attached to the 24 Volt AC-rinse cycle signal from the conventional AM-14 control panel. The first pump has zero delay with variable run time and the second pump has variable delay and run time (which would cease when the complete rinse cycle was complete). By changing the variable voltage pots on the programming board of the rinse additive dispensers, one could vary the delivery time of each pump independently. Each pump was equipped with a 2 milliliter squeeze tube and set at maximum RPM.

The delivery volume of each pump was calibrated after any change to delivery time, speed or delay. Check valves were placed in-line to minimize cross-contamination of the post detergent composition from the food grade compositions.

Chemicals
Post Detergent Compositions
Surface active agents may contain an Ethoxylated moiety

Liquid Rinse Aid A

| Ingredient | Wt % |
| --- | --- |
| Hydrophilic Mod. Siloxane | 2 |
| Glycol | 3 |
| Mixed (EO)(PO) sulfate | 37.8 |
| Linear Alcohol Ethoxylate (13 mole) | 2.5 |

-continued
Liquid Rinse Aid A

| Ingredient | Wt % |
| --- | --- |
| Dye | 0.01 |
| Antimicrobial/Biocide | 0.04 |
| HCl 20° Be | |
| Water | Bal. |

Liquid Rinse Aid B

| Ingredient | Wt % |
| --- | --- |
| Octane Sulfate | 23.5 |
| Phosphono-butane Tricarboxylic Acid-sequesrtant | 9.0 |
| (EO)(PO) Surfactant | 41.7 |
| Linear Alcohol Ethoxylate | 0.2 |
| Sodium Xylene Sulfonate Hydrotrpe/Coupler | 10.0 |
| Dye | 0.01 |
| Biocide | 0.02 |
| Water | Bal. |

Food Grade Compositions
  Surface active agents contain
Food grade chemicals

Liquid Rinse Aid D

| Ingredient | Wt % |
| --- | --- |
| Sucrose Fatty Acid Ester | 7.3 |
| Glycol | 43.8 |
| Ethanol | 1.4 |
| Sorbitan Fatty Acid Ester | 31.1 |
| Water | Bal. |

Solid Rinse Aid C

| Ingredient | Wt % |
| --- | --- |
| Sucrose Polyacid Ester | 80 |
| Sorbitan Fatty Acid Ester | 15 |
| Polyoxyethylene Sorbitan Fatty Acid Ester | 5 |

The detergent includes:

Solid Detergent

| Ingredient | Wt % |
| --- | --- |
| NaOH | 2.17 |
| Phosphonate Sequestrant | 3.14 |
| Linear Alcohol Ethoxylate | 2.55 |
| (EO) (PO) Copolymer Surfactant | 0.22 |
| Sodium Carbonate | 51.0 |
| Sodium Tripolyphosphate | 29.22 |
| (EO) (PO) Block Polymer Surfactant | 1.10 |
| Stearic Acid Mono-ethanol Amide | 0.18 |

-continued

Solid Detergent

| Ingredient | Wt % |
|---|---|
| Hydrophilic Siloxane | 0.48 |
| Water | Bal. |

These ingredients were mixed in order and then extruded to form the product which formed a solid when packaged.

Food Soil include: Standard testing soils—
  Hot point soil—4 parts by weight margarine and 1 part by weight non-fat dry milk.
  Hot point/Beef Stew/Potato soil—1 part hot point soil, 1 part canned beef stew and part dried potato buds.

Testing: To establish the utility of the food grade rinse additives versus the post detergent additives, individual sheeting tests were performed using a standard sheeting test. Sheeting test for the post detergent additives are well established. Sheeting tests for the Japanese food grade rinse additives show that in our testing range for all of the Japanese formulations, sheeting was not observed under these conditions.

An example as shown in Table 1 below, indicates typical sheeting range for Liquid Rinse Aid A which is a post detergent additive. Liquid Rinse Aid D, which is a food grade rinse additive, was tested at concentrations as high as 200 ppm, with no sheeting observed. These tests were conducted at 160° F., without suds. A lack of sheeting is indicated by "–", while pinhole sheeting is indicated by "P" and complete sheeting is indicated by "X".

Dual Rinse Additive Approach

In this case, the AM-14, specially equipped, is charged with detergent, food soil and a four second dose of post detergent additive followed by a five second dose of food grade rinse additive. In general, the use of Liquid rinse Aid A or Liquid Rinse Aid B (post detergent additives) at from 50 to 200 ppm of alkyl ethoxylated surfactant, followed by Liquid Rinse Aid D at 50 to 200 ppm food grade surfactant, gave no sheeting. Use of a post detergent additive followed by a water rinse, gave sheeting depending on delivery times.

TABLE 4

| Ppm alkaline detergent | 1000 | 1000 | 1000 | 1000 | 1000 | 1000 | 1200 | 1200 | 1200 |
|---|---|---|---|---|---|---|---|---|---|
| ppm actives (post detergent) | 50 | 100 | 150 | 100 | 200 | 150 | 50 | 100 | 0 |
| ppm ethoxylated in rinse | 0 | 0 | 0 | 0 | 0 | 0 | 50 | 100 | 0 |
| ppm food grade in rinse | 0 | 0 | 0 | 200 | 200 | 150 | 0 | 0 | 200 |
| polycarbonate bowl (clear) | — | X | X | — | — | — | — | X | — |
| glass tumbler | — | X | X | — | — | — | — | X | — |
| china plate | — | X | X | — | — | — | — | X | — |
| Dinex bowl (gray) | — | X | X | — | — | — | — | X | — |
| polysulfonate dish (clear tan) | — | X | X | — | — | — | — | X | — |
| stainless steel knife | — | X | X | — | — | — | — | X | — |

The use of a post detergent additive with Solid Rinse Aid C resulted in sheeting as indicated in the table below.

TABLE 5

| Ppm detergent | 1200 | 1200 | 1200 | 1200 | 1200 | 1200 |
|---|---|---|---|---|---|---|
| ppm actives (post detergent) | 0 | 0 | 0 | 100 | 100 | 100 |
| ppm food grade in rinse | 25 | 50 | 100 | 25 | 50 | 100 |
| polycarbonate bowl (clear) | — | P | X | — | — | X |
| glass tumbler | — | X | X | P | X | X |
| china plate | P | X | X | P | X | X |
| melamine okate | — | X | X | P | X | X |
| polypropylene plate (tan) | — | X | X | — | P | X |
| Dinex bowl (gray) | — | X | X | — | X | X |
| polysulfonate dish (clear tan) | — | X | X | — | X | X |
| stainless steel knife | P | X | X | P | P | X |

Detergent was carbonate based

TABLE 3

| ppm of sheeting agent | 0 | 10 | 20 | 30 | 40 | 50 | 60 | 70 | 80 | 90 | 100 | 110 |
|---|---|---|---|---|---|---|---|---|---|---|---|---|
| polycarbonate tile (clear) | — | — | — | — | — | X | X | X | X | X | X | X |
| polycarbonate bowl (clear) | — | — | — | — | X | X | X | X | X | X | X | X |
| glass tumbler | — | — | — | — | — | X | X | X | X | X | X | X |
| china plate | — | — | — | — | — | — | — | X | X | X | X | X |
| melamine plate | — | — | — | P | P | P | P | X | X | X | X | X |
| polypropylene plate (tan) | — | — | — | — | X | X | X | X | X | X | X | X |
| polypropylene cup (yellow) | — | — | — | X | X | X | X | X | X | X | X | X |
| Dinex bowl (gray) | — | — | — | X | X | X | X | X | X | X | X | X |
| polypropylene jug (blue) | — | — | — | X | X | X | X | X | X | X | X | X |
| polysulfonate dish (clear tan) | — | — | — | X | X | X | X | X | X | X | X | X |
| polysulfonate spoon (clear tan) | — | — | — | — | — | X | X | X | X | X | X | X |
| stainless steel knife | — | — | — | — | X | X | X | X | X | X | X | X |

TABLE 5-continued

| Ppm detergent | 1200 | 1200 | 1200 | 1200 | 1200 | 1200 |

Solid Detergent was dispensed as 40,000 ppm sump suspension
Wash cycle was 48 seconds
Post wash cycle was 4 seconds
Rinse cycle was 5 seconds at 0.5 L/sec
Solid Rinse Aid C contains 80% surface active food grade material The above specification, examples and data provide a complete description of the manufacture and use of the composition of the invention. Since many embodiments of the invention can be made without departing from the spirit and scope of the invention, the invention resides in the claims hereinafter appended

We claim:

1. A method of cleaning ware to remove any alkaline residue or residue of a synthetic nonionic sheeting agent, the cleaning method comprises the sequential steps of:
   (a) removing soil from ware by contacting said ware with an aqueous alkaline cleaning composition to produce ware having an alkaline residue;
   (b) removing said alkaline residue from said ware by contacting the ware having said alkaline residue with a first aqueous rinse composition, the first aqueous rinse composition comprising about 10 to 500 ppm of a synthetic nonionic sheeting agent comprising a polyalkylene oxide moiety to form treated ware having a synthetic nonionic sheeting agent residue;
   (c) contacting the treated ware with a second aqueous rinse composition comprising about 1 to 800 ppm of a combination of a food grade sheeting agent and a solubility agent to produce clean ware, wherein the solubility agent enhances the water-solubility of said food grade sheeting agent; and
   (d) treating said clean ware with a post-detergent sanitizing step; wherein the method removes any of the alkaline residue or the synthetic nonionic sheeting agent residue from the ware.

2. The method of claim 1 wherein the second aqueous rinse composition comprises about 1 to 400 ppm of the solubility agent and about 0.01 to 25 ppm of an acid.

3. The method of claim 1 wherein the second aqueous rinse composition comprises a surfactant composition comprising 1 to 250 ppm of a sucrose fatty acid ester, and about 1 to 320 ppm of said solubility agent, said second aqueous rinse composition having a pH of less than 7.

4. The method of claim 1 wherein the food grade sheeting agent is selected from the group consisting of a sucrose fatty acid ester, a sorbitan fatty acid ester, a glycerol fatty acid ester, a propylene glycol fatty acid ester, a soya phospholipid, and mixtures thereof.

5. The method of claim 1 wherein the food grade sheeting agent is used at a concentration of about 20 to 300 ppm.

6. The method of claim 1 wherein the food grade sheeting agent is used at a concentration of about 25 to 150 ppm.

7. The method of claim 1 wherein the solubility agent is selected from the group consisting of ethanol, propylene glycol, glycerol and mixtures thereof.

8. The method of claim 1 wherein the ware is contacted with the aqueous rinse composition for about 3 to 7 seconds.

9. The method of claim 1 wherein the ware is contacted with the aqueous rinse composition for about 4 to 6 seconds.

* * * * *